United States Patent
Granot et al.

(10) Patent No.: US 7,505,135 B2
(45) Date of Patent: Mar. 17, 2009

(54) METHOD AND APPARATUS FOR IMAGING THROUGH SCATTERING OR OBSTRUCTING MEDIA

(75) Inventors: Er'el Granot, Herzlia (IL); Shmuel Sternklar, Rehovot (IL)

(73) Assignee: Ariel Ltd., Ariel (IL)

( * ) Notice: Subject to any disclaimer, the term of this patent is extended or adjusted under 35 U.S.C. 154(b) by 356 days.

(21) Appl. No.: 10/521,533

(22) PCT Filed: Jul. 14, 2003

(86) PCT No.: PCT/IL03/00582

§ 371 (c)(1),
(2), (4) Date: Nov. 7, 2005

(87) PCT Pub. No.: WO2004/008116

PCT Pub. Date: Jan. 22, 2004

(65) Prior Publication Data

US 2006/0146331 A1    Jul. 6, 2006

(51) Int. Cl.
*C07K 14/705* (2006.01)

(52) U.S. Cl. .................................. 356/432; 356/451

(58) Field of Classification Search ................. 356/432
See application file for complete search history.

(56) References Cited

U.S. PATENT DOCUMENTS 5,734,470 A * 3/1998 Rogers et al. ............... 356/502
6,456,380 B1 * 9/2002 Naganuma ................. 356/450
6,853,455 B1 * 2/2005 Dixon et al. ............... 356/453
2001/0038454 A1 * 11/2001 Tsuchiya .................... 356/432

OTHER PUBLICATIONS

V. Tuchin, "Tissue optics", (SPIE Press, 2000).
B.B. Das, F. Liu and R.R. Alfano, Rep. Prog. Phys. 60, 227 (1997) "Time-resolved fluorescence and photon migration studies in biomedical and model random media".
J.C. Hebden, "Evaluating the spatial resolution performance of a time-resolved optical imaging system" Med. Phys. 19, 1081 (1992).
Q.Z. Wang, X. Liang, L. Wang, P.P. Ho, and R.R. Alfano, "Fourier spatial filter acts as a temporal gate for light propagating through a turbid medium", Optics Letters, 20, 1498 (1995).
E. N. Leith et al, "Realization of time gating by use of spatial filtering", Appl. Opt. 38, 1370 (1999).
A. Kuditcher et al, "Ultrafast cross correlated harmonic imaging through scattering media", Appl. Opt. 40, 45 (2001).

(Continued)

*Primary Examiner*—L. G Lauchman
*Assistant Examiner*—Rebecca C Slomski
(74) *Attorney, Agent, or Firm*—Alston & Bird LLP

(57) ABSTRACT

Method and system for determining the optical temporal response of a medium (12) to a short optical pulse excitation, by sending light (11) that comprises spectral frequencies which make up the Fourier Transform of the short pulse to be emulated through the medium. The relative amplitude and phase change (20) of each of the spectral components light (14) exiting the medium is determined with respect to that of the illuminating light source and the spectral response of the medium is obtained from the relative amplitude and phase change. An inverse Fourier Transform is then computationally performed on the spectral response to obtain the temporal response of the medium to the emulated short pulse.

16 Claims, 6 Drawing Sheets

OTHER PUBLICATIONS

A. Yodh and B. Chance, "Spectroscopy and Imaging with Diffusing Light", Physics Today, pp. 34-40, Mar. 1995.

H. Jiang et al, "Optical image reconstruction using frequency-domain data : simulations and experiments", JOSA A13, 253 (1996).

T.O. McBride et al, "Initial studies of in-vivo absorbing and scattering heterogeneity in near-infrared tomographic breast imaging", Opt. Lett. 26, 822 (2001).

Arons and Dilworth, "Analysis of Fourier synthesis holography for imaging through scattering materials", Appl. Opt. 34, 1841 (1995).

Zhang, K. & Lilge, L.: "Frequency-domain near infrared . . . amplifier", Conference on Lasers & Electro Optics Cleo '99. Opt.Soc.Am., May 23-28, 1999, pp. 251-252, XP002260523.

* cited by examiner

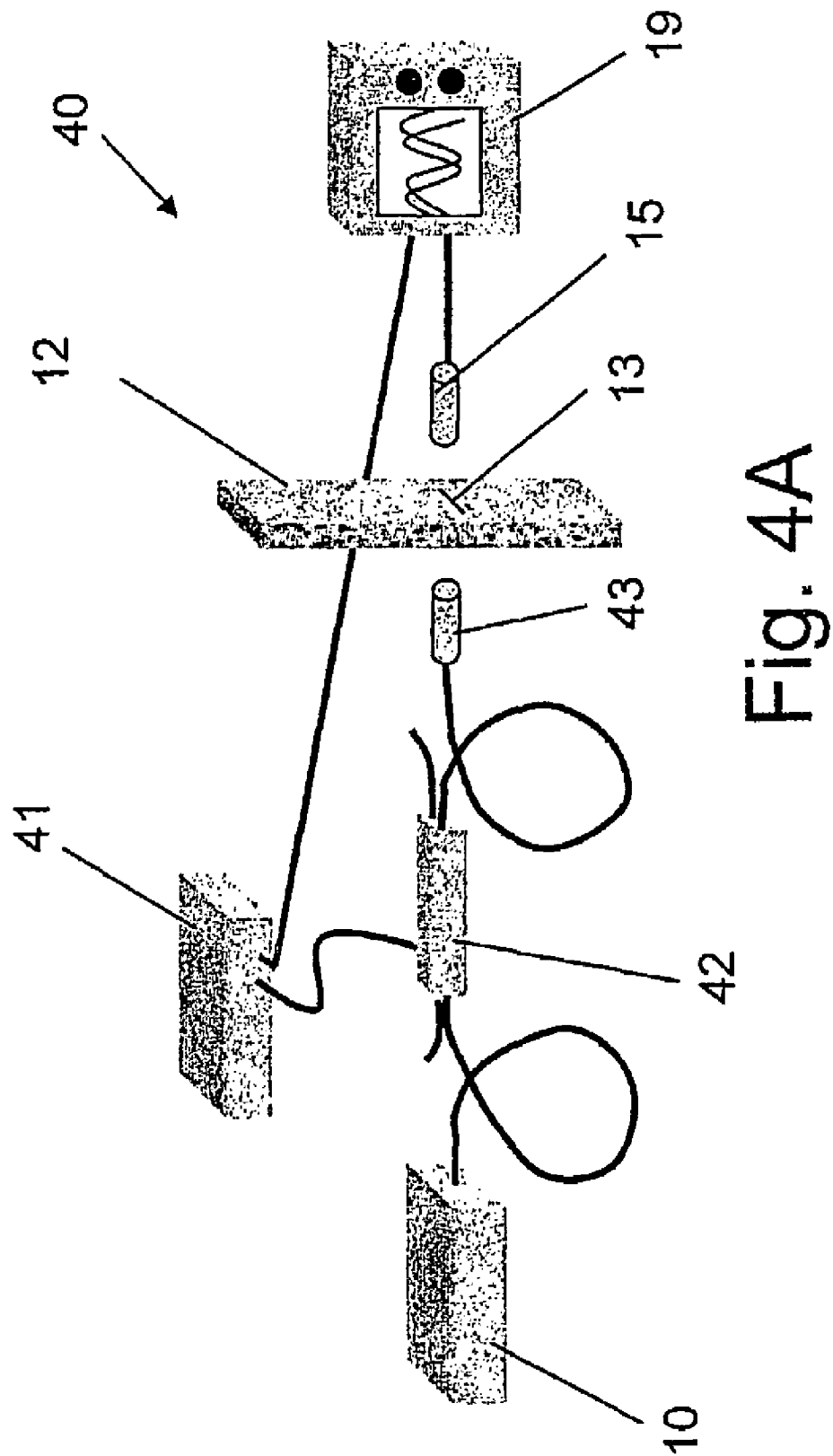

METHOD AND APPARATUS FOR IMAGING THROUGH SCATTERING OR OBSTRUCTING MEDIA

FIELD OF THE INVENTION

The invention relates to the field of optical imaging. Specifically the invention relates to methods and apparatus for determining the optical temporal response of a medium to a short optical pulse excitation.

BACKGROUND OF THE INVENTION

Publications and other reference materials referred to herein, including references cited therein, are incorporated herein by reference in their entirety and are numerically referenced in the following text and respectively grouped in the appended Bibliography, which immediately precedes the claims.

There are many applications that would benefit from a noninvasive optical means of viewing objects embedded within turbid media or otherwise obstructed by other objects. In military and security applications the ability to see through obstructions or turbidity is of great importance for example for detecting the presence of concealed weapons under clothing or viewing enemy forces concealed by fog or cloud cover.

In medical diagnostics the most common methods for diagnosing abnormalities of internal organs are based on circumstantial evidence. For example, high cholesterol levels in the blood might be circumstantial evidence for vascular diseases. Obviously, the physician can use endoscopes to obtain a much better perspective of the extent of the disease. The ability to "see" the organ, i.e., to measure its optical properties, results in a wealth of clinical information. The reason for this is that most of the biological molecules absorb light in the optical regime of the spectrum. Therefore, it is relatively simple to distinguish between different biological tissues with optical devices. However, endoscopy and similar procedures are invasive methods and therefore cannot be used in many cases or as frequently as the physician would like.

For these reasons, noninvasive methods were developed to diagnose internal organs. However there exist few, if any reliable noninvasive techniques to measure the optical properties of these internal organs. As a consequence, most of the ubiquitous methods rely on circumstantial evidence for diagnosing the internal abnormalities. For example, in x-ray mammography most of the tumor findings are due to the presence of micro-calcifications, which gives only circumstantial evidence of the tumor's presence.

The inability to see through biological tissue is only a specific example of a broad family of related problems pointing to the apparent futility of using optical radiation for direct imaging through a turbid or obstructing medium. This problem is ubiquitous in everyday life. Fog, clouds, turbid water, and milk are just a few examples from everyday encounters with such optically turbid media. In particular, biological media are highly diffusive for visible and infrared light. As a result, an optical image is severely deteriorated, even after passing through a few millimeters of tissue.

Despite this severe shortcoming, it is clear that a reliable non-invasive optical technique would be a very useful clinical tool in diagnosing in-vivo internal organs. Moreover, the use of light as a diagnostic tool has many advantages over other non-invasive diagnostic techniques. Unlike x-rays, light is not oncogenic, it has the potential of giving a much higher resolution than ultrasound imaging, and the required equipment is potentially much cheaper than MRI. These benefits and technological progress in optical equipment have encouraged researchers to develop optical diagnostic tools for turbid biological systems.

Although many methods based on coherence, polarization, diffusion properties etc. have been developed [1], two techniques appear to be the most promising: the time-domain and frequency-domain techniques. [Other techniques, such as optical coherence tomography, which utilizes short-coherence-length light, can be regarded as equivalent to the short pulse illumination method.]

The most direct and one of the most popular approaches to seeing through a turbid medium is the first-light or time-domain technique. In this method the first arriving light, which contains the undistorted image, is separated from the scattered light by a very fast time-gating camera [2-6]. In ref. 3, the authors suggest that a resolution of a few millimeters is achievable in a system with a temporal resolution of about 10 ps. This method demands complex and very expensive equipment.

While the time-domain technique gives superfluous information, and the requirement of the measurement equipment is to distinguish between the informative (i.e., ballistic) portion of the signal and the noise (i.e. diffusive portion), the frequency-domain techniques usually results in less information. In the frequency-domain approach [1, 7-9] the laser light is RF modulated (MHz-GHz), and the measurement of the amplitude and phase of the modulated diffusive light take place at the boundaries of the medium. Then, a numerical reconstruction takes place in which the light distribution in the medium is calculated from the collected data.

The frequency-domain technique is considered to be simpler, more reliable and more economic than the time-domain method, since it needs much simpler equipment. Moreover, unlike the time-domain method, the detected signal in this technique can be considerably stronger since it includes the entire signal energy, not merely the ballistic or quasi-ballistic portion, which can be quite small in a highly turbid medium, In principle, the two methods are equivalent since the latter one can be regarded as the Fourier counterpart of the former. However, except for small technical details, the main difference between the two is the spectral range. In the time-domain techniques (for medical purposes) pulses of about a few picoseconds are used, which is equivalent to a spectral range of more than 100 GHz. However it is difficult to modulate light at frequencies greater than 10 GHz. Therefore the concept is different: instead of collecting the data in time, in the frequency-domain method the data is collected in space (on the medium's boundaries). Such a method requires complicated numerical algorithms, is sensitive to boundary conditions, and its spatial resolution is limited by the medium's diffusion length.

It is therefore a purpose of the present invention to provide a method for determining the optical temporal response of a medium to a short optical pulse excitation, at least a portion of which is indicative of the position and shape of an object or objects embedded in an optically turbid medium and/or obstructed by other objects that are at least partially transparent.

It is another purpose of the present invention to provide a method for determining the optical temporal response of a medium to a short optical pulse excitation, at least a portion of which is indicative of the position and shape of an object or objects embedded in an optically turbid medium and/or obstructed by other objects, that can be carried out without using short pulses and fast detectors.

It is a further purpose of the present invention to provide a method for determining the optical temporal response of a medium to a short optical pulse excitation, at least a portion of which is indicative of the position and shape of an object or objects embedded in an optically turbid medium and/or obstructed by other objects, that can be carried out with relatively inexpensive equipment.

Further purposes and advantages of this invention will appear as the description proceeds.

SUMMARY OF THE INVENTION

The present invention relates to providing a method, which will be called herein Spectral Ballistic Imaging (SPEBI), of computationally deriving the ballistic photon (or "first light") image after characterizing the optical spectral transfer function of the medium in a suitably wide spectral band and with suitable spectral resolution. Let $f_{in}(t)$ describes a short pulse which, in the prior art method, would be sent through the medium in a 'ballistic' imaging system, and $f_{out}(t)$ is the output which would be obtained and would contain the information on the ballistic and 'first light' response, as well as the light which would arrive later due to scattering. In the present invention, the Fourier transform $E_{in}(\omega)$ of the short input pulse is sent instead. The output spectrum $E_{out}(\omega)$ is measured, giving the medium's transfer function $H(\omega)$. By determining this spectral transmission response of the medium with a suitable resolution, an inverse Fourier transform operation will allow the determination of the short pulse response $f_{out}(t)$ In this way the 'fate' of the ballistic photons can be determined and a high-resolution image can be achieved. This invention allows for trans-illumination imaging through a scattering volume, or reflection-illumination imaging through discrete scattering layers.

In a first aspect, the present invention is directed towards a method for determining the optical temporal response of a medium to a short optical pulse excitation. The method comprises sending light comprising spectral frequencies, which make up the Fourier transform of the short pulse to be emulated through the medium. The relative amplitude and phase change of each of the spectral components light exiting the medium is determined with respect to that of the illuminating light source and the spectral response of the medium is obtained from the relative amplitude and phase change. An inverse Fourier transform is then computationally performed on the spectral response to obtain the temporal response of the medium to the emulated short pulse. The light can be either CW (Continuous Wave) or modulated. The method can be carried out using light that comprises only part of or substantially all of the spectral frequencies which make up the Fourier transform of the short pulse to be emulated. The method can be carried out by using light which has a carrier frequency that is scanned over time; and the relative amplitude and phase change are determined for each carrier frequency. The method can also be carried out using light consisting of a broad spectral bandwidth and each of the spectral components of the output of the light exiting the medium is detected.

The light can be detected either at a point, along a line, or over a two-dimensional area. The medium can comprise discrete layers. The detected light can be either transmitted through the medium, reflected back from the medium, or exit the medium at any angle with respect to the illumination path. There can be at least one object embedded within the medium which can be detected and imaged. The at least one object can comprise a cancerous growth or other undesirable physiological formation, and the medium comprises a segment of the human body.

The 'first light' response, or other specific segment of the temporal response, which is indicative of the position and shape of the object or objects embedded in an optically turbid medium and/or obstructed by other objects, which are at least partially transparent, cab be determined from the optical temporal response.

In another aspect, the present invention is directed towards a system for determining the optical temporal response of a medium to a short optical pulse excitation. The system is comprised of a tunable laser, an RF oscillator, modulating means, detecting means, an optically scattering medium, electronic processing means, and optional optical elements means.

All the above and other characteristics and advantages of the invention will be further understood through the following illustrative and non-limitative description of preferred embodiments thereof with reference to the appended drawings.

BRIEF DESCRIPTION OF THE DRAWINGS

FIG. 4A schematically shows the experimental setup for a SPEBI experiment to detect the ballistic light response through diffuse glass and a hidden object.

DETAILED DESCRIPTION OF PREFERRED EMBODIMENTS

In this specification the terms "turbid medium", "scattering medium", "optically scattering medium", "optically turbid medium", and other terms having a similar meaning are used interchangeably.

Figure 1:
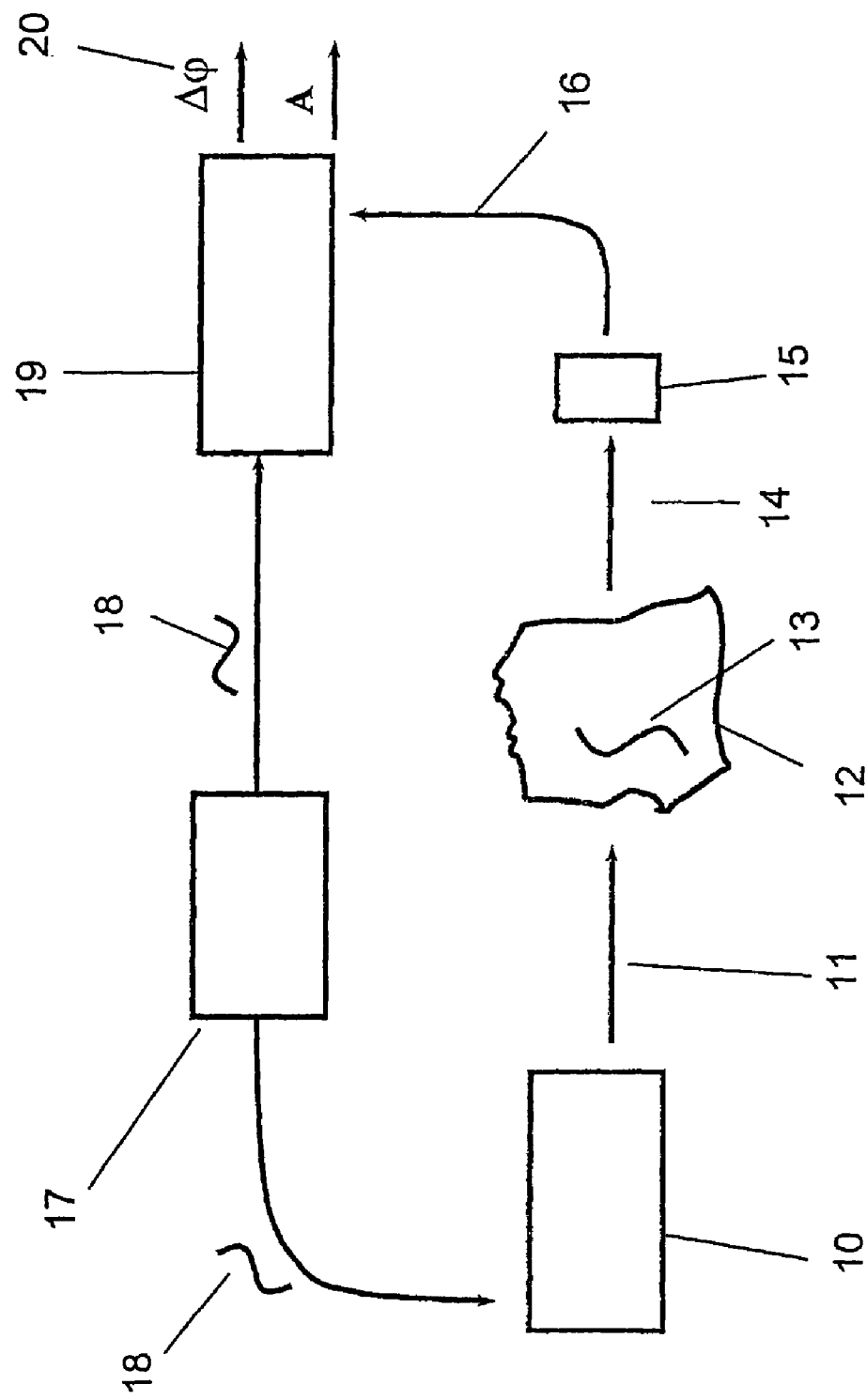
FIG. 1 schematically shows the SPEBI system in a transmission configuration.

FIG. 1 describes a transmission system used for seeing through a turbid optical medium to acquire an image of an object obscured by the medium. In the preferred embodiment shown in FIG. 1, a CW frequency-tunable laser 10 is modulated at an RF frequency $\Omega$ through the use of a RF modulation source 17, which modulates the laser with the electronic sinusoidal signal 18. In the weak modulation regime, the modulated light field 11 is $$E_{in}(t, \omega_j) \cong e^{i\omega_j t}(1 + a\cos\Omega t) = e^{i\omega_j t}\left[1 + \frac{a}{2}(e^{i\Omega t} + e^{-i\Omega t})\right] \quad [1A]$$

where $\omega_j$ is the optical carrier frequency and $\alpha \ll 1$ (for simplicity, unit amplitude at the carrier frequency is assumed). It should be noted that the weak modulation regime is neither an essential nor a simplifying assumption; similar conclusions are obtained for deep modulation, where expression (1) takes a simpler form $$E_{in}(t,\omega_j) \cong e^{i\omega_j t}(e^{i\Omega t} + e^{-i\Omega t}). \quad [1B]$$

Going back to the weak modulation case, the intensity is $$I_{in}(t) \cong 1 + 2\alpha\cos\Omega t. \quad [2]$$

where higher orders of the small term $\alpha$ were neglected.

A portion of this beam is directed through the turbid medium 12, which includes an embedded object 13. The output field 14 is:

$$E_{out}(t, \omega_j) = A(\omega_j)e^{i\omega_j t}\left[e^{i\varphi_j^0} + \frac{a}{2}\left(e^{i(\Omega t + \varphi_j^{(+)})} + e^{-i(\Omega t - \varphi_j^{(-)})}\right)\right]. \quad [3]$$

The added phases $\phi_j^0$, $\phi_j^{(+)}$ and $\phi_j^{(-)}$ for the three spectral components at $\omega_j$, $\omega_j + \Omega$ and $\omega_j - \Omega$ respectively, are due to the effective optical path length difference at these three frequencies. These path length differences are mainly due to material dispersion and frequency-dependent scattering paths. The factor $A(\omega_j)$ represents frequency-dependent attenuation and is real-valued. For simplicity, it is assumed for now that this factor is constant over the frequency range $\omega_j \pm \Omega$. The phases as well as the amplitude can also change due to the electronic system, cables, detector, etc., however these factors are independent of the scattering medium and embedded objects, so that they are determined and accounted for. Therefore, the output intensity at 14 which is detected by detection system 15 is $$I_{out}(\omega_j) \cong A^2(\omega_j) \cdot [1 + 2\alpha c \cos(\Omega t + \Delta\phi(\omega_j))], \quad [4]$$

where $$\Delta\varphi(\omega_j) \equiv \frac{\varphi_j^{(-)} - \varphi_j^{(+)}}{2} \text{ and } c \equiv \cos\left(\varphi_j^0 - \frac{\varphi_j^{(+)} + \varphi_j^{(-)}}{2}\right). \quad [5]$$

Electronic processor 19 compares RF signals $I_{out}$ (Eq. 4, 16 in the figure) to $I_{in}$ (Eq. 2, 18 in the figure), so that the amplitude and phase values $A(\omega_j)$ and $\Delta\phi(\omega_j)$ (20 in the figure) can be determined. 19 can be a phase detector, network analyzer, lock-in amplifier, or other electronic processor known in the art.

The laser frequency is tuned in steps of $\delta\omega$ over a frequency range $\Delta\omega$ and the values of $A(\omega_j)$ and $\Delta\phi(\omega_j)$ are acquired for every frequency $\omega_j$.

Figure 3:
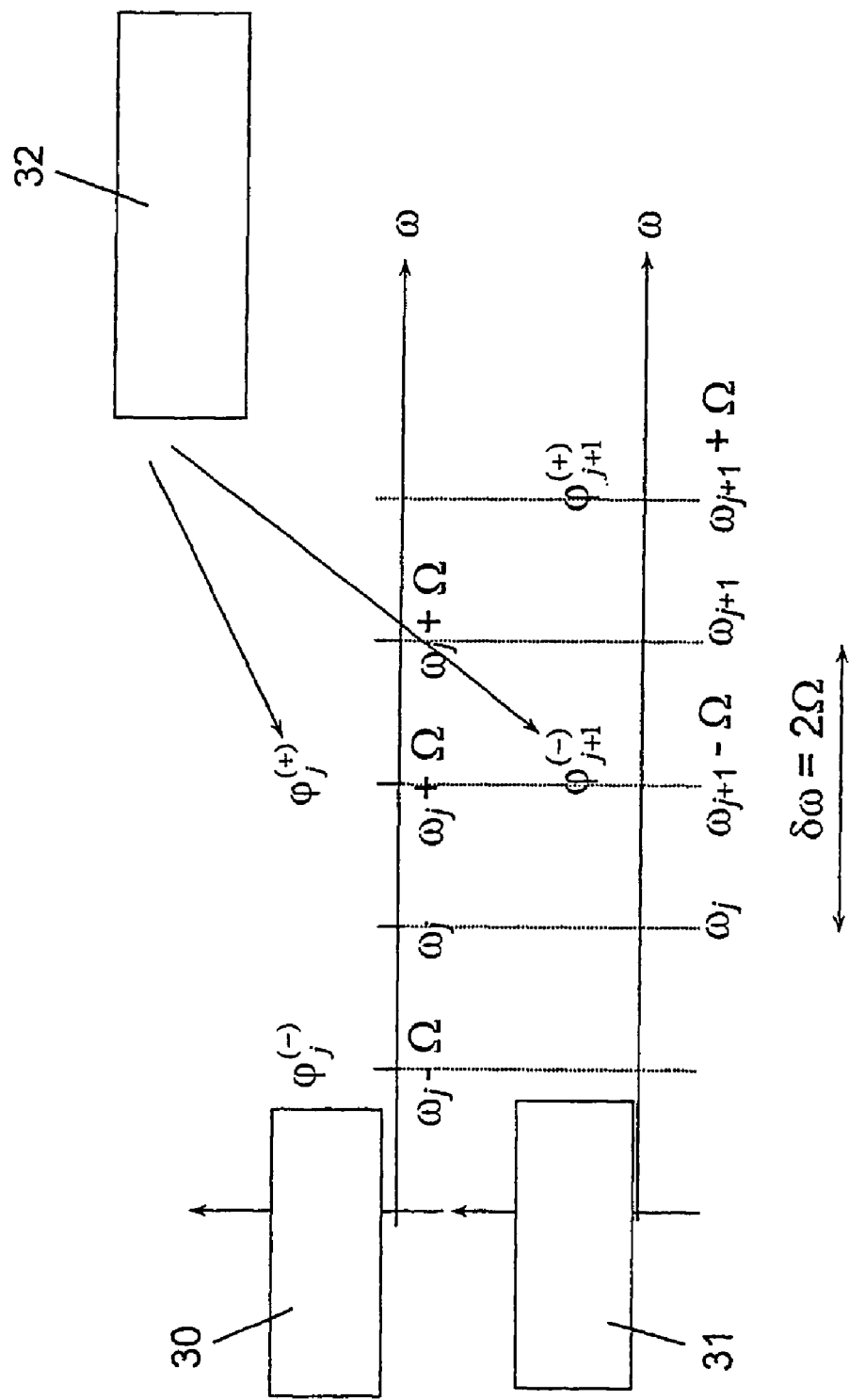
FIG. 3 schematically shows the modulation and frequency scanning scheme for a preferred embodiment of the SPEBI system.

FIG. 3 schematically shows the modulation and frequency scanning scheme for a preferred embodiment of the SPEBI system. In the figure the top line 30 shows the phases of the jth step and the bottom line 31 the phases of the (j+1)th step. The arrows 32 show that $\phi_j^{(+)} = \phi_{j+1}^{(-)}$ for every step j If the frequency steps $\delta\omega$ fulfill the relation shown in FIG. 3, i.e.

$$\delta\omega = 2\Omega \quad [6]$$

then, the spectral response of the medium, within the range $\Delta\omega$, can be determined unambiguously:

$$H(\omega_j) = A(\omega_j)e^{i\varphi(\omega_j)}, \quad [7]$$

$$\text{where } \varphi(\omega_j) = 2\sum_{m=0}^{j} \Delta\varphi(\omega_m) - \Delta\varphi(\omega_o) - \Delta\varphi(\omega_j) \quad [8]$$

is the accumulated phase, and $\omega_0$ is the lowest laser frequency to be used.

If the frequency steps are larger, i.e. $\delta\omega > 2\Omega$, Eq. (8) should be interpolated:

$$\varphi(\omega_j) = \left[2\sum_{m=0}^{j} \Delta\varphi(\omega_m) - \Delta\varphi(\omega_o) - \Delta\varphi(\omega_j)\right]\frac{\delta\omega}{\Omega}. \quad [9]$$

In the above derivation, it is assumed that the amplitudes $A(\omega_j)$ are constant over the frequency range $\omega_j \pm \Omega$. This is not a necessary requirement. If they differ, then the output intensity (Eq. 4) will have a dc value and a peak-to-peak ac value, which is dependent on the amplitudes, so that the amplitude values can be determined from a measurement of the dc and peak-to peak values.

Referring to Eq. 4, it is to be noted that the phase variable c, which affects the modulation depth of the modulated light at the output, is also dependent upon the added phases of the spectral components. Therefore, the phases $\phi(\omega_j)$ can also be determined by measuring the modulation depth of the output signal.

A computational inverse Fourier transform of $H(\omega)$ will give the temporal response of the medium to an input pulse whose spectral bandwidth is $\Delta\omega$. The 'first-light' signal can be extracted from this information by computationally filtering out the bulk of the temporal response and retaining the 'first-light' response (in analogy to the task of the fast shutter in a real short-pulse measurement). Note that the computational work, which may form the bulk of the acquisition time, can be done 'off-line', either simultaneously, or after the spectral data is collected.

Other holographic methods [10] are in some sense similar to aspects of the current invention, since in both methods the measurements are done in the spectral domain, and both amplitude and phase are measured. However, there are two crucial differences between the two techniques: 1) The holography methods are based on interference of two beams that pass through two totally different trajectories. This type of interferometric measurement is highly sensitive to system noise, and difficult to implement in non-laboratory systems. In the present invention, on the other hand, the two beams copropagate along common paths, and therefore the measurement is extremely robust; 2) Moreover, since in both methods the phase and amplitude must be measured, the methods of Arons et al [10] consists of two scans: wavelength and time delay, while the present invention requires only a wavelength scan, since the measurements of amplitude and phase are done simultaneously.

Figure 2:
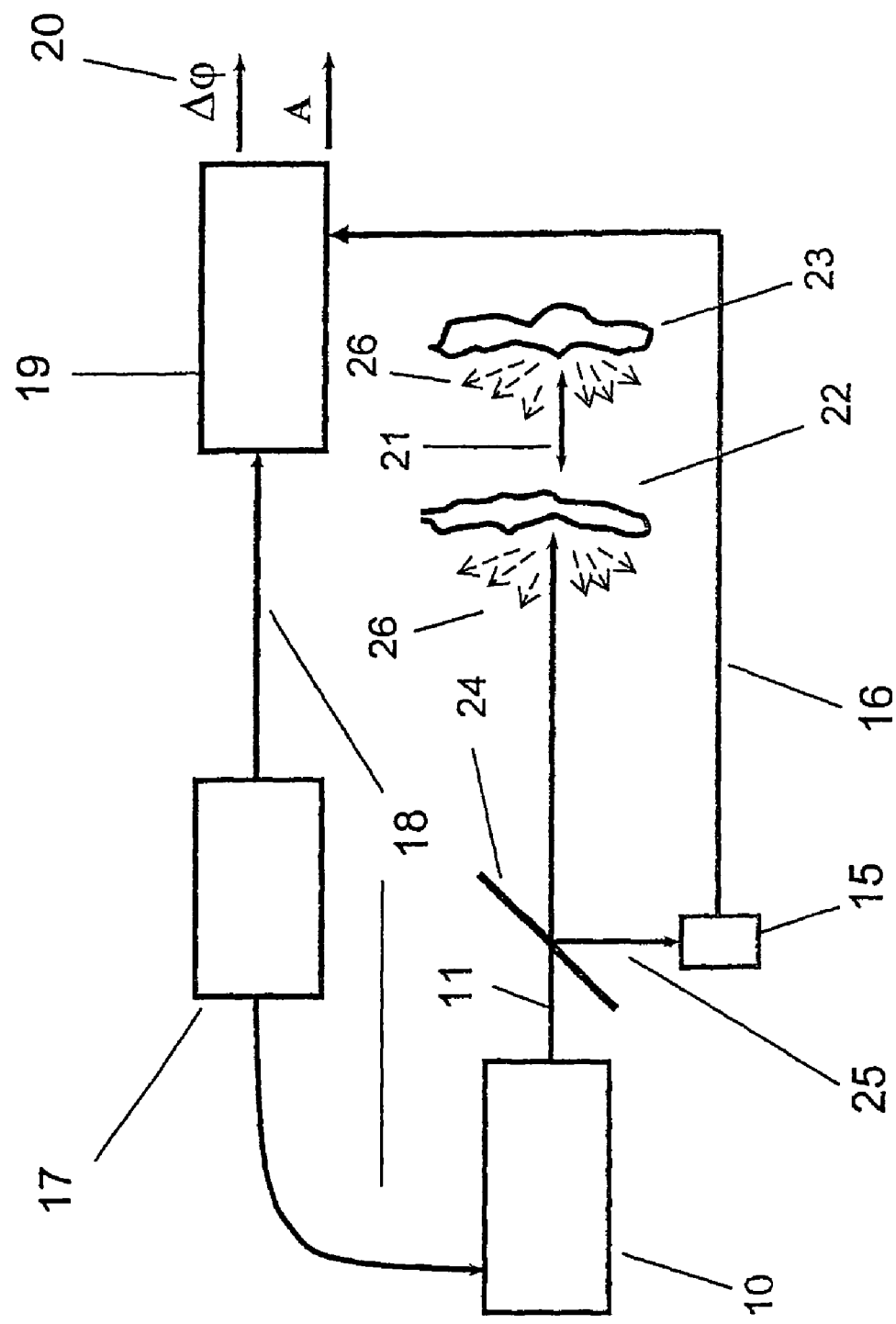
FIG. 2 schematically shows the SPEBI system in a reflection configuration.

FIG. 2 shows schematically a preferred embodiment for acquiring the image of an object obscured by an absorbing layer in a reflection-illumination configuration. Elements 10, 11, 15, 16, and 17 to 20 are identical to those of FIG. 1. In FIG. 2, the laser output 11 is directed towards a target, which consists of multiple scattering layers, two are depicted in the figure as 22 and 23. Layer 23 is also the object, hidden behind the front scattering layer 22. A portion of the light 21 transverses the first layer and is reflected back by the object at small enough angles with respect to the optical axis that it is collected by the detection system. Much of the light is scattered in a wide angle by all of the layers, shown as 26. A beam splitter 24 deflects the returning light 25 into detector 15.

The laser modulation and signal processing is identical to that of FIG. 1. As in the transmission case, the temporal response is computed, and the 'first light' response is determined, so that the image information of the hidden object can be extracted.

As in time-gated imaging, as well as other imaging techniques, it is difficult to extract information on objects deeply embedded within a scattering volume when using the reflection configuration. This is due to the accumulated backscattering of light from the scattering volume in front of the object, which is usually much stronger than the ballistic back-reflection from the desired object. Therefore, SPEBI, like other first-light techniques, works best with discrete scattering layers, as shown in FIG. 2, or in situations where the objects are not deeply embedded within the scattering volume. The ballistic light, which is reflected from each layer would appear temporally separated, so that the information on the object layer can be extracted.

Acquisition of a complete two-dimensional (2D) image of the desired object requires the computation of the ballistic light components within the entire 3D volume. This can be done by scanning the input light and detector throughout the 2D input and output planes, and performing the SPEBI measurements for each coordinate. Alternatively, the entire input plane of the scattering medium can be illuminated simultaneously, while performing parallel measurements using a detector array at the output plane. The light sources and/or detectors may include lenses, optical fiber, mirrors or other optical components for light expansion, collection, focusing, steering, etc. as is well-known in the art.

The above discussion leads to the conclusion that the main parameters to be determined to enable the SPEBI measurements to be carried out are the desired spectral resolution $\delta\omega$, laser modulation frequency $\Omega$ and the required tuning range $\Delta\omega$. These parameters and the method used to determine them will now be discussed.

The tuning range is optimally the spectral bandwidth of the input pulse width $\tau_p$, which is to be emulated with the tunable CW laser. A good rule of thumb is that for a dense optical medium of length l, the pulse width should be significantly smaller than the 'flight time' of a ballistic photon $T_B=nl/c$ through the medium, so that $\tau_p \approx 0.01$ nl/c, where n is the effective index of refraction. Assuming a Gaussian pulse, so that $\Delta\omega=4/\tau_p$, gives $\Delta\omega=400$ c/nl. The required spectral resolution $\delta\omega$ is dependent upon the characteristic diffusion time of the medium. In order to obtain full reconstruction the spectral resolution of the measurement should be better than $\delta\omega \approx 2\pi/T_D$ where $T_D$ is the diffusion time, which can be approximated by $T_D \cong l^2/D \cong 3 \mu_s' nl^2/c$. D is the diffusion constant and $\mu_s'$ is the effective scattering coefficient (the reciprocal of the random walk length). As an example, for ordinary human tissues $T_D \cong 10$ ns.

Assuming 100 resolution points, or $\Delta\omega/\delta\omega \geq 10^2$, gives $\delta\omega=4$ c/nl and $\Omega=2$ c/nl. Assuming, for example, a length of 10 cm and n=1.5, leads to the following required operating parameters for a tunable laser with a center wavelength of 1530 nm: a wavelength tuning range of 1.0 nm, tuning resolution of 10 pm, and modulation frequency of 640 Mhz. This will emulate the performance of a 5 ps laser pulse.

Tunable lasers having these parameters are commercially available. For example, the TUNICS-PRI-1530 supplied by NetTest Photonics fulfills the above requirements. This laser has the following specifications: wavelength tunability range 1480-1580 nm, wavelength resolution=1 pm, and power modulation frequency $\Omega/2\pi$ up to 1 GHz. The tuning range of 100 nm means that a minimum pulse length of approx. 50 fs can be emulated. The 1 pm resolution capability means that the lowest $\delta\omega/2\pi=128$ MHz and that up to $10^5$ resolution points can be measured. Skilled persons will realize that the number of resolution points can be lowered to a limit where $\delta\omega/2\pi=2\Omega/2\pi=2$ GHz.

An important advantage of the tunable laser is the ease with which its power can be amplified. Since it operates at the optical communication wavelength band and is fiber-coupled, its power can be easily (and relatively cheaply) amplified from 3 mW to over 500 mW using an Erbium-doped fiber amplifier (EDFA). For medical and other applications, it may be advantageous to employ wavelengths in the 800 nm-900 nm band. Other types of tunable laser sources, e.g. Ti:Sapp., diode lasers, that are known in the art can be used in SPEBI.

Alternatively, a broadband light source of bandwidth $\Delta\omega$ can be used to illuminate the sample; while, at the output, the detector system includes a means of spectrally separating the light components and measuring the amplitude and phase of each spectral component.

The actual number of resolution points that will be required in a given type of medium may be lower, and in certain circumstances significantly lower than the result of the above model. For example, if a priori information regarding the medium's optical characteristics is known, then the number of resolution points can be decreased. In many circumstances, interpolation of the missing data would be sufficient. In certain applications, a data bank of spectral data, e.g. data on breast tissue with and without cancerous growths, could be used in order to efficiently categorize the data of a particular patient, so that a high-resolution measurement would not be required.

In FIG. 4A is schematically shown the SPEBI set-up 40 for an experiment designed to measure the time response of opal diffuse glass 12, behind which was place a small absorbing object 13. The glass was illuminated with light from a tunable laser 10 of the type described above. The effective input pulse length was 1.5 ps, the modulation frequency was 1 Ghz, and the thickness of the glass was 3 mm. Also shown in FIG. 4A are RF oscillator 41, modulator 42, optional optical elements 43, detector 15, and electronic processor 19 which provides the amplitude and phase data.

Figure 4B:
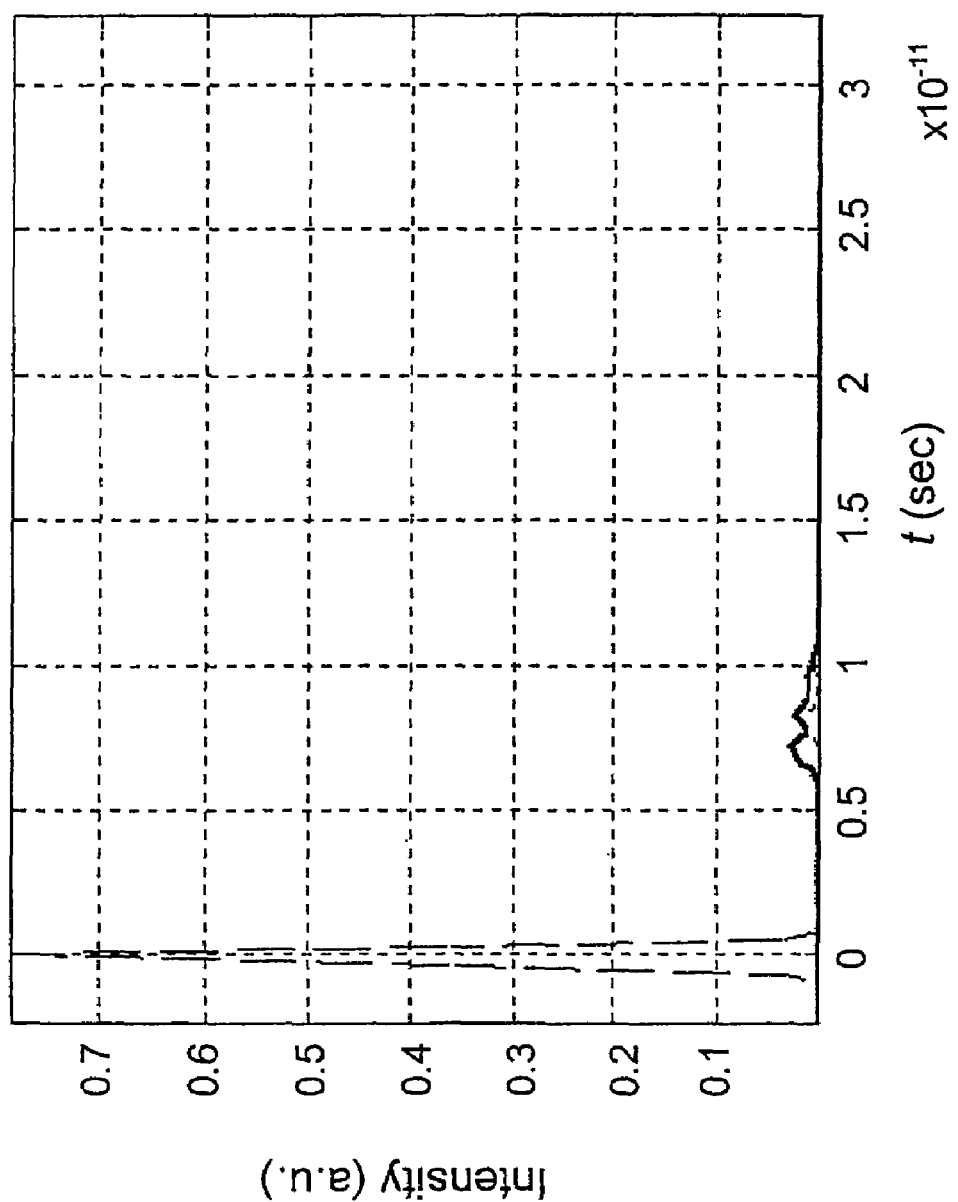
FIGS. 4B and 4C show the results of the SPEBI experiment of FIG. 4A.

FIG. 4B shows the reconstructed time response of the medium, with and without the absorber, to an input pulse of 1.5 ps shown at t=0. According to the method of the invention, it is not this pulse, but its Fourier transform that is transmitted through the diffusing medium and the object. The inverse Fourier transform of the recorded data is then calculated and it is this that is known as the reconstructed optical response of the diffusing medium and the absorbing object which appears between 0.5 and $1.1 \times 10^{-11}$ seconds after the initial pulse.

Figure 4C:
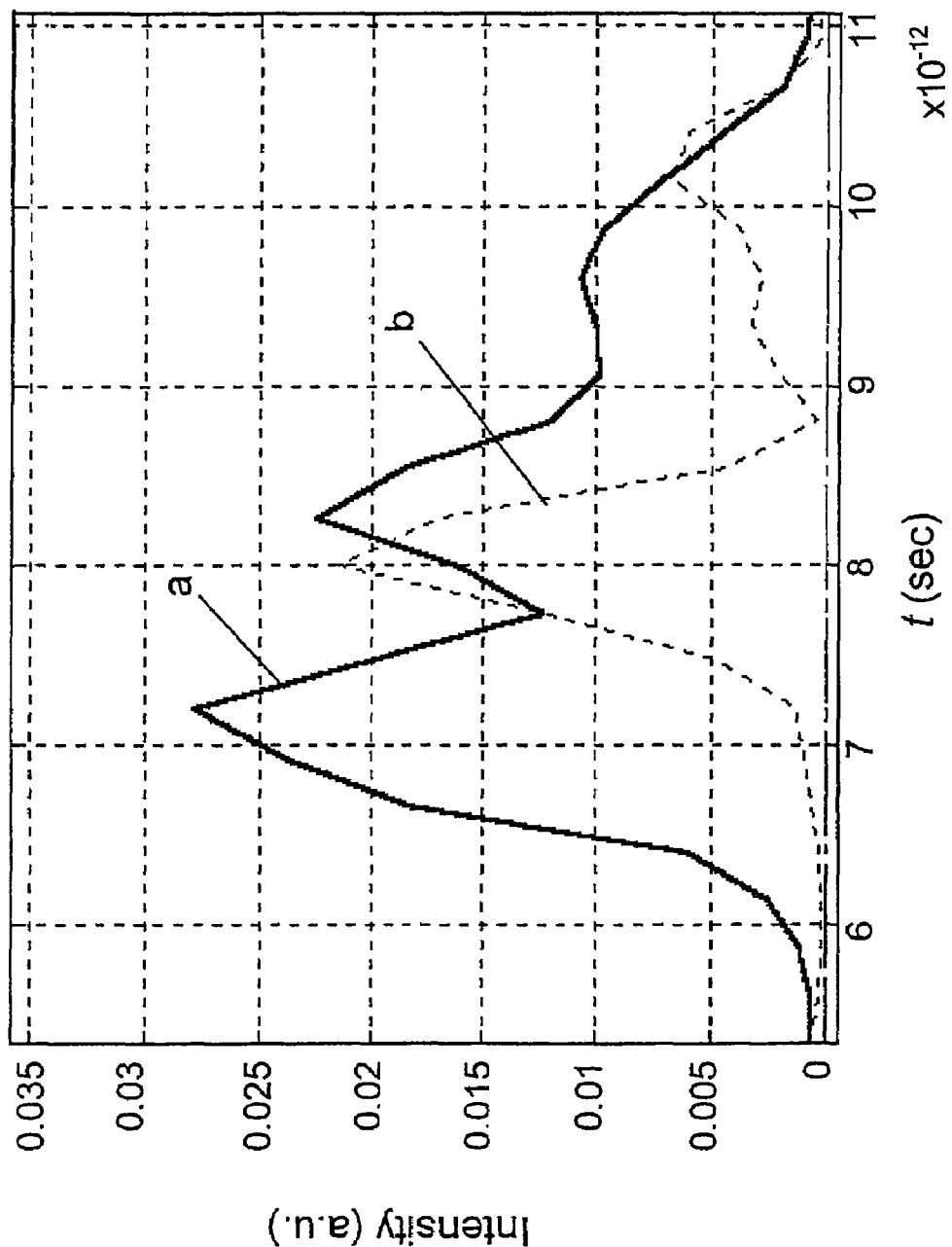

FIG. 4C is an enlargement of the features shown between 0.5 and $1.1 \times 10^{-11}$ seconds in FIG. 4B. In FIG. 4C, curve a is the reconstructed optical response of the medium alone and curve b that of the medium with the absorber. Curve b has been magnified by a factor of 7. In the reconstructed optical responses, pulse expansion and deformation due to the scattering medium is clearly seen. In addition, it can be seen how the absorber has blocked the first-arriving light. This experiment demonstrates that a temporal resolution of less than ~1 ps is easily achievable; that it is possible to separate the ballistic and quasi ballistic ("snake photons") portion of the signal from the diffusive component; that an obstructed object can be detected; and, perhaps most importantly, that a relatively noiseless signal can be obtained with this technique.

Although embodiments of the invention have been described by way of illustration, it will be understood that the invention may be carried out with many variations, modifications, and adaptations, without departing from its spirit or exceeding the scope of the claims.

BIBLIOGRAPHY

[1] V. Tuchin, "*Tissue optics*", (SPIE Press, 2000).
[2] B. B. Das, F. Liu and R. R. Alfano, Rep. Prog. Phys. 60, 227 (1997) "Time-resolved fluorescence and photon migration studies in biomedical and model random media".
[3] J. C. Hebden, "Evaluating the spatial resolution performance of a time-resolved optical imaging system" Med. Phys. 19, 1081 (1992).
[4] Q. Z. Wang, X. Liang, L. Wang, P. P. Ho, and R. R. Alfano, "Fourier spatial filter acts as a temporal gate for light propagating through a turbid medium", Optics Letters, 20, 1498 (1995).
[5] E. N. Leith et al, "Realization of time gating by use of spatial filtering", Appl. Opt. 38, 1370 (1999).
[6] A. Kuditcher et al, "Ultrafast cross correlated harmonic imaging through scattering media", Appl. Opt. 40, 45 (2001).
[7] A. Yodh and B. Chance, "Spectroscopy and Imaging with Diffusing Light", Physics Today, pp. 34-40, Mar. 1995.
[8] H. Jiang et al, "Optical image reconstruction using frequency-domain data: simulations and experiments ", JOSA A13, 253 (1996)
[9] T. O. McBride et al, "Initial studies of in-vivo absorbing and scattering heterogeneity in near-infrared tomographic breast imaging", Opt. Lett. 26, 822 (2001).
[10] Arons and Dilworth, "Analysis of Fourier synthesis holography for imaging through scattering materials", Appl. Opt. 34, 1841 (1995).

The invention claimed is:

1. A non-interferometric method for determining the optical temporal response of an optically scattering medium to a short optical pulse excitation, said method comprising the following steps:
   (a) sending a modulated beam of light from a light source through said medium, wherein said light is comprised of at least some of the spectral frequencies which make up the Fourier transform of said short optical pulse;
   (c) measuring, for each of said spectral components, the relative amplitude with respect to that of said light source;
   (c1) measuring, for each of said spectral components, the difference between the modulation phase of said light exiting said medium and the modulation phase of said modulated beam of light entering said medium;
   (c2) determining, the phase change of the optical field of each of said spectral components with respect to that of said light from said light source entering the medium from the values of the difference between the modulation phase of said light exiting said medium and the modulation phase of said modulated beam of light entering said medium;
   (d) obtaining the spectral response of said medium from said relative amplitude changes and optical field phase changes;
   (e) computationally performing an inverse Fourier transform on said spectral response; and
   (f) obtaining the temporal response of said medium to said emulated short pulse from said inverse Fourier Transform; and
   (g) repeating step (a) through (f) until said optical temporal response is determined to a pre-determined accuracy, wherein the light sent through said medium in each succeeding cycle is at least partially comprised of different spectral frequencies from those of the preceding cycles;
   characterized in that the relative amplitude and phase change of each of said spectral components with respect to that of said light source are determined from a single beam of modulated light.

2. A method according to claim 1, wherein the light comprises substantially all of the spectral frequencies, which make up the Fourier transform of the short pulse to be emulated.

3. A method according to claim 1, wherein the light comprises substantially less than all of the spectral frequencies which make up the Fourier transform of the short pulse to be emulated.

4. A method according to claim 1, wherein the light has a carrier frequency, which is scanned over time; and the relative amplitude and phase change are determined for each carrier frequency.

5. A method according to claim 1, wherein the light consists of a broad spectral bandwidth and each of the spectral components of the output of said light exiting the medium are detected.

6. A method according to claim 1, wherein the light is detected either at a point, along a line, or over a two-dimensional area.

7. A method according to claim 1, wherein the light transmitted through the medium is detected.

8. A method according to claim 1, wherein the light reflected back from the medium is detected.

9. A method according to claim 1, wherein the light, which exits the medium at any angle with respect to the illumination path, is detected.

10. A method according to claim 1, wherein at least one object is embedded within the medium.

11. A method according to claim 10, wherein the at least one object is detected.

12. A method according to claim 10, wherein the at least one object is imaged.

13. A method according to claim 10 where the at least one object comprises biological tissue and the medium comprises a segment of the human body.

14. A method according to claim 1, wherein the medium comprises discrete layers.

15. A method according to claim 1, wherein a 'first light' response, which is indicative of the position and shape of an object or objects embedded in an optically scattering medium and/or obstructed by other objects, which are at least partially transparent, is determined from the optical temporal response.

16. A method according to claim 1, wherein a specific segment of the temporal response, which is indicative of the position and shape of an object or objects embedded in an optically scattering medium and/or obstructed by other objects, which are at least partially transparent, is determined from said optical temporal response.

* * * * *

UNITED STATES PATENT AND TRADEMARK OFFICE
CERTIFICATE OF CORRECTION

PATENT NO. : 7,505,135 B2  Page 1 of 1
APPLICATION NO. : 10/521533
DATED : March 17, 2009
INVENTOR(S) : Granot et al.

It is certified that error appears in the above-identified patent and that said Letters Patent is hereby corrected as shown below:

Title Page,

Insert the following:

-- Related U.S. Application Data

(60) Provisional application No. 60/395,282, filed on Jul. 15, 2002 --.

Signed and Sealed this

Ninth Day of June, 2009

JOHN DOLL
*Acting Director of the United States Patent and Trademark Office*